(12) United States Patent
Stergiopulos et al.

(10) Patent No.: US 10,596,035 B2
(45) Date of Patent: Mar. 24, 2020

(54) APPARATUS FOR TREATING EXCESS INTRAOCULAR FLUID

(71) Applicant: ÉCOLE POLYTECHNIQUE FÉDÉRALE DE LAUSANNE (EPFL), Lausanne (CH)

(72) Inventors: Nikolaos Stergiopulos, Préverenges (CH); Constantinos Stergiopulos, Préverenges (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 361 days.

(21) Appl. No.: 15/612,988

(22) Filed: Jun. 2, 2017

(65) Prior Publication Data
US 2017/0348149 A1    Dec. 7, 2017

Related U.S. Application Data

(60) Provisional application No. 62/346,456, filed on Jun. 6, 2016.

(51) Int. Cl.
*A61F 9/00* (2006.01)
*A61F 9/007* (2006.01)
*A61M 27/00* (2006.01)

(52) U.S. Cl.
CPC ........ *A61F 9/00781* (2013.01); *A61F 9/0017* (2013.01); *A61M 27/002* (2013.01); *A61F 9/00736* (2013.01); *A61F 2250/0013* (2013.01)

(58) Field of Classification Search
CPC ............. A61F 9/00781; A61F 9/0017; A61F 9/00736; A61F 2250/0013; A61M 27/002; A61M 27/006; A61M 27/008
See application file for complete search history.

(56) References Cited

U.S. PATENT DOCUMENTS

| | | |
|---|---|---|
| 3,863,067 A | 1/1975 | Gooley |
| 4,232,451 A | 11/1980 | Thomsen |
| 4,457,757 A | 7/1984 | Molteno |
| 4,856,972 A | 8/1989 | Van Benschoten et al. |
| 5,117,870 A | 6/1992 | Goodale et al. |

(Continued)

FOREIGN PATENT DOCUMENTS

| | | |
|---|---|---|
| EP | 1 243 826 | 9/2002 |
| EP | 1 484 535 A1 | 12/2004 |

(Continued)

OTHER PUBLICATIONS

International Search Report & Written Opinion dated Mar. 29, 2012 in Int'l PCT Patent Application No. PCT/EP2012/050455.

(Continued)

*Primary Examiner* — Philip R Wiest
(74) *Attorney, Agent, or Firm* — Eversheds Sutherland (US) LLP; Christopher C. Bolten; Nicola A. Pisano

(57) ABSTRACT

Apparatus and methods are provided for treating diseases that produce elevated intraocular pressures, such as glaucoma, wherein the device operates on the principles of a Starling resistor, and includes a housing, a deformable structure and a spring mounted within a housing, such that the spring applies a substantially constant spring force over a predetermined working range on the deformable structure to thereby self-regulate flow of fluid through the deformable structure.

20 Claims, 8 Drawing Sheets

(56) References Cited

U.S. PATENT DOCUMENTS

| | | |
|---|---|---|
| 5,300,020 A | 4/1994 | L'Esperance, Jr. |
| 5,342,025 A | 8/1994 | Hwang |
| 5,411,473 A | 5/1995 | Ahmed |
| 5,586,872 A | 12/1996 | Skobelev et al. |
| 5,601,094 A | 2/1997 | Reiss |
| 5,626,558 A | 5/1997 | Suson |
| 6,050,970 A | 4/2000 | Baerveldt |
| 6,077,299 A | 6/2000 | Adelberg et al. |
| 6,168,575 B1 | 1/2001 | Soltanpour |
| 6,186,974 B1 | 2/2001 | Allan et al. |
| 6,261,256 B1 | 7/2001 | Ahmed |
| 6,450,984 B1 | 9/2002 | Lynch et al. |
| 6,508,779 B1 | 1/2003 | Suson |
| 6,544,208 B2 | 4/2003 | Ethier et al. |
| 6,589,198 B1 | 7/2003 | Soltanpour et al. |
| 6,726,664 B2 | 4/2004 | Yaron et al. |
| 7,093,818 B2 | 8/2006 | Koeneman |
| 7,854,600 B2 | 12/2010 | Ogawa |
| 9,101,445 B2 | 8/2015 | Bigler et al. |
| 9,655,779 B2 | 5/2017 | Bigler et al. |
| 2002/0087111 A1 | 7/2002 | Ethier et al. |
| 2004/0162545 A1 | 8/2004 | Brown et al. |
| 2005/0053501 A1 | 3/2005 | Akahori |
| 2007/0154336 A1 | 7/2007 | Miyazaki et al. |
| 2008/0228127 A1* | 9/2008 | Burns .............. A61F 9/00781 604/9 |
| 2009/0099626 A1 | 4/2009 | De Juan et al. |
| 2009/0208350 A1 | 8/2009 | Miyazaki et al. |
| 2010/0321345 A1 | 12/2010 | Pearce et al. |
| 2011/0066098 A1 | 3/2011 | Stergiopulos |

FOREIGN PATENT DOCUMENTS

| | | |
|---|---|---|
| JP | 54-007791 | 1/1979 |
| JP | 06-509732 | 11/1994 |
| JP | 10-503405 | 3/1998 |
| JP | 2004-340184 | 12/2004 |
| WO | WO-91/12037 A1 | 8/1991 |
| WO | WO-93/03778 A1 | 3/1993 |
| WO | WO-96/03944 A1 | 2/1996 |
| WO | WO-99/62586 A1 | 12/1999 |
| WO | WO-99/66862 A1 | 12/1999 |
| WO | WO-2009/066133 A1 | 5/2009 |
| WO | WO-2014/036437 A1 | 3/2014 |

OTHER PUBLICATIONS

Sponsel, et al., Retrobulbar Diversion of Aqueous Humor: Clinical Feasibility Studies, J. Glaucoma, 23(9):628-632 (2014).

International Search & Written Opinion dated Sep. 14, 2017 in Int'l PCT Patent Appl. Serial No. PCT/IB2017/053294.

Johnstone, et al., Aqueous Veins and Open Angle Glaucoma, The Glaucoma Book: A Practical, Evidence-Based Approach to Patient Care, Chapter 7, pp. 65-78 (2010).

Kiel, Jeffrey W., Ocular Perfusion Pressure, I0P and the Ocular Starling Resistor Effect, The Ocular Circulation, p. 13-16, Dec. 31, 2010.

U.S. Appl. No. 13/349,353 / U.S. Pat. No. 9,101,445, filed Jan. 12, 2012 / Aug. 11, 2015.

U.S. Appl. No. 14/819,286 / U.S. Pat. No. 9,655,779, filed Aug. 5, 2015 / May 23, 2017.

U.S. Appl. No. 15/600,597, filed May 19, 2017.

* cited by examiner

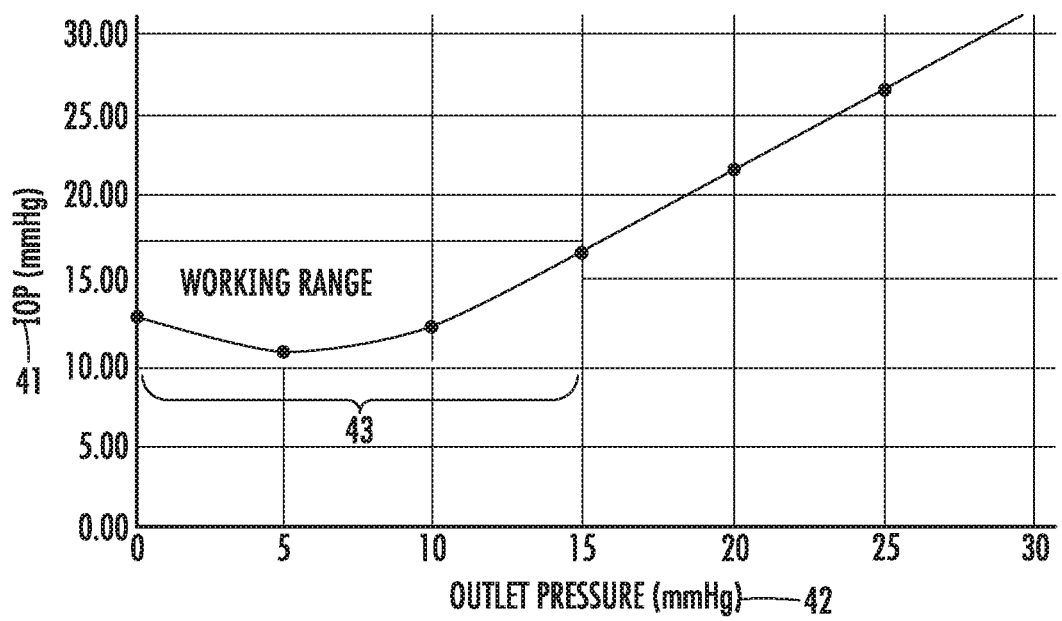
FIG. 6
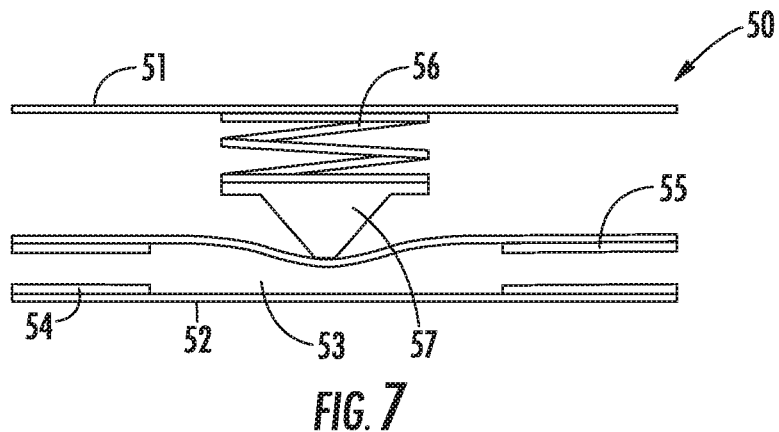
FIG. 7
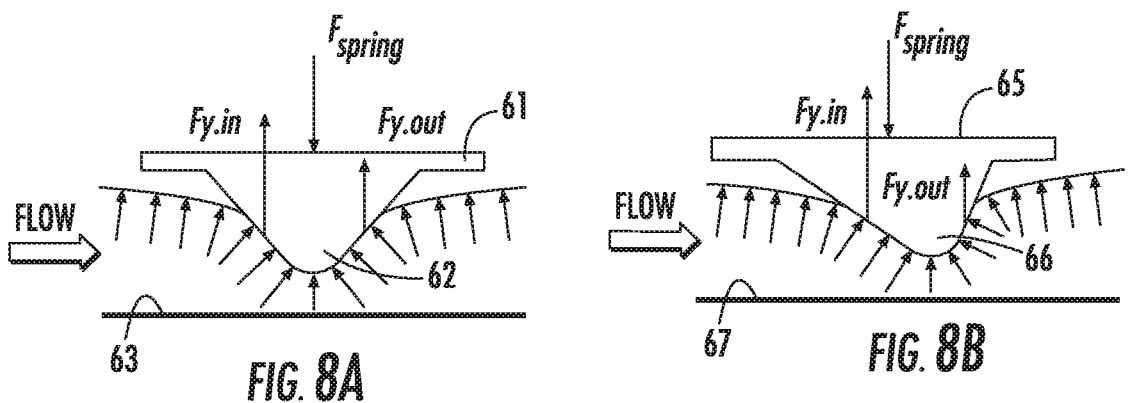
FIG. 8A
FIG. 8B

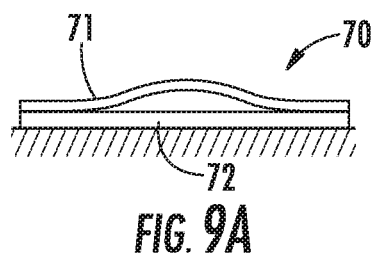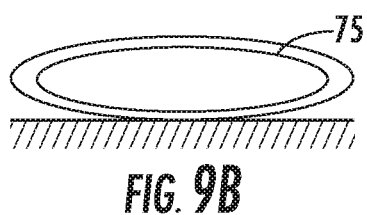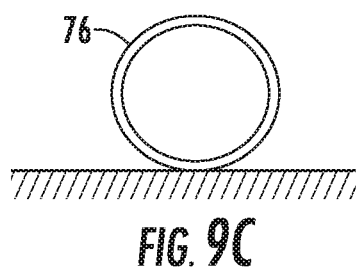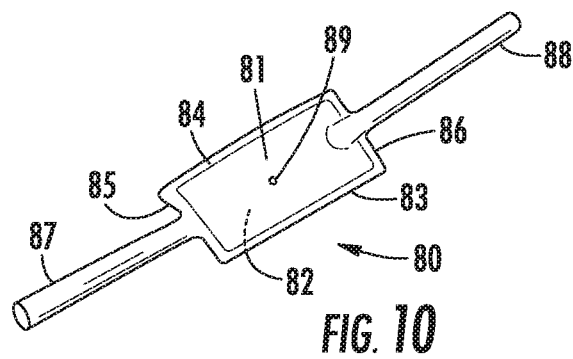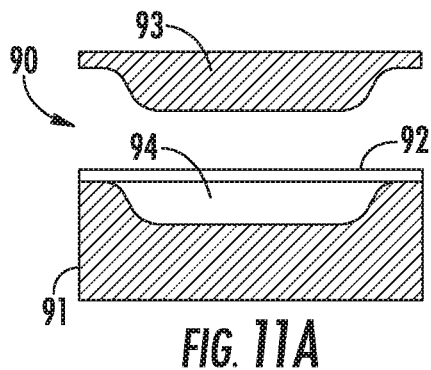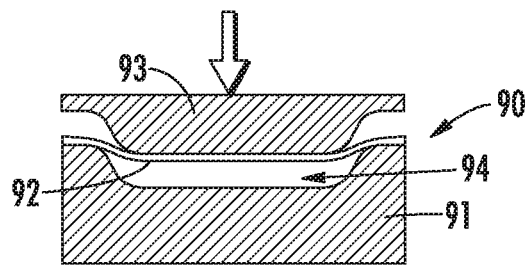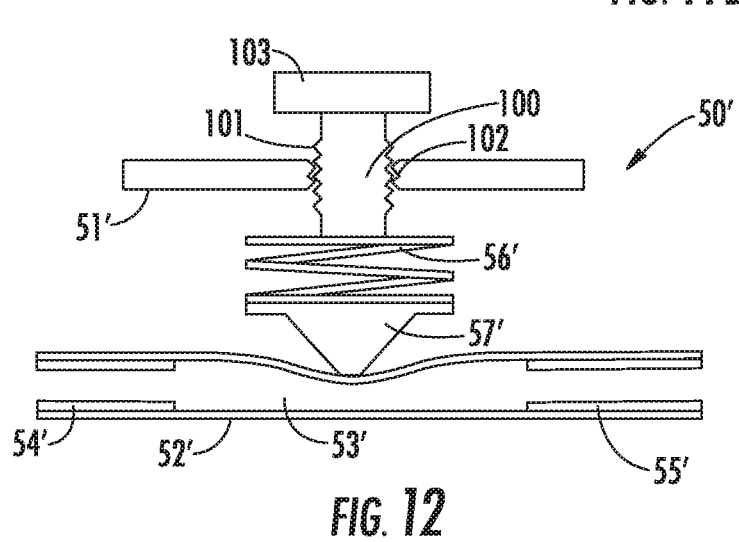

APPARATUS FOR TREATING EXCESS INTRAOCULAR FLUID

CROSS-REFERENCE TO RELATED APPLICATIONS

This application claims the benefit of priority of U.S. Provisional Application No. 62/346,456, filed Jun. 6, 2016, the entire contents of which are incorporated by reference.

FIELD OF INVENTION

This application relates to an apparatus for draining excess intraocular fluid to relieve intraocular pressure, for example, for treating glaucoma.

BACKGROUND OF THE INVENTION

Glaucoma affects about 70 million people worldwide, and is a disorder associated with high pressure in the eye resulting from the generation of excess intraocular fluid (aqueous humor). Aqueous humor is produced at a rate of 2-3 µl/min by the ciliary body and in a normal human eye maintains a constant intraocular pressure ("IOP") around 12-20 mmHg. Aqueous humor exits the eye primarily through the trabecular meshwork and Schlemm's canal, where it eventually drains to the episcleral veins. Maintaining intraocular pressure within appropriate ranges is critical to health of the eye, and depends on aqueous humor dynamics, namely the production rate from the ciliary body (aqueous humor inflow) and its outflow rate through the trabeculum. The most frequent type of glaucoma, called open-angle glaucoma, results from an increase in the fluidic resistance of the trabecular meshwork. Left untreated, this disease typically causes damage to the optic nerve, with consequent loss of vision, initially peripheral, but progressively leading to total blindness. Unfortunately, glaucoma is often asymptomatic until late in the progress of the disease.

Traditionally, glaucoma is treated using medication, for example, the daily application of eye drops, such as Brinzolamide ophthalmic, that reduce production of aqueous humor. Such medications do not cure glaucoma, and must be continue to be taken to maintain intraocular pressures within accepted limits. In certain cases, such treatment may fail and other surgical treatments are employed, such as filter procedures or placement of a glaucoma drainage device. Glaucoma drainage devices reduce intraocular fluid pressure by providing an artificial drainage pathway, thus maintaining a low IOP.

Previously-known glaucoma drainage devices usually comprise a structure having a drainage tube that is inserted through a small incision made in the conjunctiva. The surgeon makes a tiny incision in the sclera of the eye and creates an opening for the drainage implant device. The drainage tube is placed such that the opening of the tube is disposed in the anterior chamber of the eye within the aqueous humor. The tube is sutured in place with the drainage device attached to the sclera of the eye. Many surgeons will place an absorbable suture around the tube at the time of surgery to prevent over-filtration through the device until a fibrous capsule has formed. Accordingly, such devices typically are not functional until about 3 to 8 weeks after the procedure, so as to prevent over-filtration.

An exemplary previously-known passive glaucoma drainage device is described in U.S. Pat. No. 4,457,757 to Molteno. The device described in that patent comprises a tube of a biologically inert silicone configured to be inserted into the eye to drain aqueous humor from the anterior chamber of the eye. The device does not include a pressure regulating mechanism, but instead relies on the resistance to aqueous flow through the tubing to prevent over drainage.

One drawback of devices such as those described in the Molteno patent is that the drainage flow depends on IOP and on the fixed hydrodynamic resistance of the shunt. In many cases, however, the hydrodynamic resistance of the shunt may not be sufficient to reduce high IOP when the resistance to flow is too high, or may lead to over-drainage if the resistance is low. For example, a common problem, which arises shortly after implantation, is hypotony, which occurs when IOP drops below acceptable physiological levels (i.e., IOP<10 mmHg). Hypotony usually takes place the first few days to weeks following the implantation of a glaucoma drainage device, and is a combined result of a low fluidic resistance of both the implant and the distal outflow paths. Hypotony may lead to a number of undesirable effects and complications, such as hypotensive maculopathy, cataract formation and optic nerve edema. Another problem, also related to the fixed fluid resistance of previously known implants, is fibrosis, which appears progressively at long term and which, depending on its extent and severity, may raise the effective fluidic resistance of the implant, thereby raising the TOP to different, often non-physiological, levels.

The foregoing drawbacks have been recognized in the prior art, and several improvements have been attempted to improve flow control over the entirely passive system described in Molteno.

For example, U.S. Pat. No. 5,411,473 to Ahmed describes a drainage device that includes a membrane-type valve. More specifically, Ahmed describes a drainage system including a membrane folded and held in tension between two plates to provide a slit opening, such that the membrane responds to pressure changes to open or close the slit opening. Unfortunately, the operational characteristics of the system depend on the properties of the membrane, which cannot be changed easily once the device is implanted. Also, the valve of Ahmed does not provide a true opening pressure to accurately control post-operation TOP.

U.S. Pat. No. 6,544,208 to Ethier describes a self-regulating pressure system. More specifically, Ethier describes an implantable shunt device having a flexible tube positioned in a pressurized enclosure. In this patent, flow through the tube is dependent on a differential pressure between a pressure in the flexible tube and a pressure outside the flexible tube in the pressurized enclosure. However, one skilled and experienced in the field of medical implants, especially in ophthalmology, would understand that such a system with a constant external pressure chamber would be very impractical, if not impossible, to make.

Ethier further describes that the pressure outside the flexible tube in the pressurized enclosure of the implantable shunt device is generated by osmotic effects. More specifically, the pressurized enclosure is filled with a solution containing a solute that generates an osmotic pressure which controls the opening pressure of the implantable shunt device. The implantable shunt device includes a semi-permeable membrane affixed between support gratings that reduce deformation of the semi-permeable membrane. Unfortunately, significant deformation of the semi-permeable membrane makes it difficult to predict the osmotic pressure within the pressurized enclosure.

U.S. Pat. No. 9,101,445 to Bigler describes an ocular drainage system for treating diseases that produce elevated intraocular pressures, such as glaucoma, wherein the system includes an implantable device and an external control unit.

The implantable device includes a non-invasively adjustable valve featuring at least one deformable tube and a disk rotatably mounted within a housing, such that rotation of the disk using the external control unit causes the disk to apply a selected amount of compression to the deformable tube, thereby adjusting the fluidic resistance of the deformable tube and regulating the intraocular pressure.

Still other examples of previously-known systems are known. U.S. Pat. Nos. 5,626,558 and 6,508,779 to Suson describe a shunt which may be adjusted after implantation by using a low power laser to drill additional openings in the tube wall to adjust the flow rate. U.S. Pat. No. 6,186,974 to Allan et al. describes a drainage shunt having multiple layers, one of which may be a gel that swells upon absorption of fluid to adjust flow rate through the tube. U.S. Pat. No. 6,726,664 to Yaron describes a drainage tube including a distal hook that retains the distal end of the implant within the anterior chamber of the eye, and various means, such as rods or sutures, for partially occluding the lumen of the tube to regulate flow.

Other previously-known glaucoma treatment systems include significantly greater complexity to address the drawbacks of the simpler shunt systems described above. For example, U.S. Pat. No. 6,077,299 to Adelberg, et al. describes a non-invasively adjustable valve implant for the drainage of aqueous humor for treatment of glaucoma, wherein an implant having an inlet tube is surgically inserted in the anterior chamber of the eye to allow aqueous humor to flow from the anterior chamber to a valve. After passing through a pressure and/or flow regulating valve in the implant, the fluid is dispersed along the periphery of the implant to the interior of the Tenon's capsule where it is absorbed by the body. In one embodiment, the valve inhibits flow below, and allows flow above, a specific pressure difference between the TOP within the eye and the pressure within the bleb cavity in the Tenon's capsule. The specified pressure difference or set-point is always positive and the valve is always closed in the presence of negative pressure differences, to prevent reverse flow of fluid from the Tenon's capsule back into the anterior chamber of the eye.

In Adelberg, the valve is formed by a chamber to which the inlet tube is connected, such that the chamber is closed by a pressure sensitive valve in the shape of a flat cone. The pressure regulation set point of the valve is governed by a flexible diaphragm that cooperates with an armature plate having an inclined surface, and which is configured to slide over a complementary inclined surface attached to the diaphragm. Cooperation of the inclined surface of the plate and the complementary surface causes the diaphragm to deflect depending on where the armature plate is located. The armature plate is rotated, using a rotor and a set of speed-reducing and torque-enhancing gears, to regulate the flow through the device. The characteristics of the valve strongly depend on the configuration of the cone shaped valve. In addition, the regulating mechanism is complex, including many rotating parts and gears, and this complexity poses a risk of malfunction.

In view of the drawbacks of the foregoing prior art devices and methods, it would be desirable to provide an ocular drainage system and methods that are capable of maintaining a constant, or nearly constant, IOP.

It further would be desirable to provide an ocular drainage system effective to prevent hypotony post-implantation and/or effective in light of the development of fibrosis at long term.

It further would be desirable to provide an ocular drainage system having few moving parts, thereby enhancing robustness of the system and reducing the risk of failure arising from operation of complex mechanisms.

It further would be desirable to provide an ocular drainage system having a small volume to facilitate implantation of the device beneath the conjunctive, either under a relatively small scleral flap or on the scleral surface, or even within a diffuser plate.

It further would be desirable to provide an ocular drainage system wherein moving parts of the system are configured to reduce the risk of clogging or seizing due to the buildup of proteinaceous sediments.

Finally, it would be desirable to provide an ocular drainage system that permits the hydraulic resistance of the system to be dynamically adjusted in a non-invasive manner.

SUMMARY

The present invention overcomes the drawbacks of previously-known ocular drainage systems by providing an implantable device based upon the concept of the Starling resistor: a device that self-regulates pressure and flow, thereby avoiding hypotony and enabling TOP to be maintained within desired limits over extended periods. In alternative embodiments constructed in accordance with the principles of the present invention, the device may be non-invasively adjusted post-implantation to control the fluidic resistance of the device according to patient need.

The foregoing advantages are achieved by providing a device for the treatment of excess fluid within an eye having a housing configured to be implanted beneath conjunctiva, either beneath or above the scleral surface, or disposed within a diffuser plate, at least one deformable structure disposed within the housing, and a spring having a substantially constant spring force over a predetermined working range. The deformable structure has a lumen defining a flow area, a first end configured to be disposed in fluid communication with an anterior chamber of the eye and a second end configured to be disposed beneath or within the sclera, connected to a Seton tube, connected to a drainage tube, connected to a drainage tube coupled to a diffuser plate, or disposed completely within a diffuser plate. The deformable structure may be a soft, flexible, biocompatible material, e.g., a thermosetting polymer. The spring is mounted within the housing so that an end of the spring imposes, directly or indirectly a substantially constant force on the deformable structure that causes self-regulation of fluid flow through the deformable structure. In accordance with one aspect of the invention, the spring force applied to the deformable structure establishes a balance between an external pressure at the second end and an internal pressure of the eye at the first end.

The implantable housing may be configured to be implanted under a scleral flap and may include an inlet port and an outlet port, such that the deformable structure extends between the inlet port and outlet port. The inlet port may include a nozzle configured to pass through a wall of the eye to communicate with the anterior chamber of the eye. The outlet port may be configured so that fluid exits the outlet port beneath the scleral flap. In an alternative embodiment, the implantable housing may be configured to be implanted above the scleral surface and under the conjunctiva of the eye. In this embodiment, preferably there is a protective patch disposed on top of the implantable housing to protect the conjunctival layer from device-induced erosion. Preferably, the outlet port of the implantable housing may be connected to a Seton tube coupled to a diffuser plate. In another preferred embodiment, the outlet port of the implantable housing may be connected to a drainage tube. For example, the drainage tube may have a proximal end that may be coupled to the second end of the deformable structure, a distal region having one or more drainage holes that may be disposed within a space, e.g., the orbital fat space, of the eye, and a lumen extending between the proximal end and the one or more drainage holes. In one embodiment, the drainage tube may be coupled to a diffuser plate having a groove sized and shaped to receive a portion of the drainage tube between the proximal end and the one or more drainage holes of the drainage tube, such that the diffuser plate may be implanted beneath the conjunctiva and above a sclera. In yet another alternative embodiment, the implantable housing may be configured to be disposed completely within a diffuser plate.

The implantable housing is formed from a biocompatible material, and may include eyelets that facilitate suturing the implantable housing in position. Preferably, the implantable housing has a radius of curvature selected to accommodate the radius of curvature of a patient's eye, e.g., the radius of curvature of the implantable housing may be in a range of about 10 mm to 12 mm. Preferably, the implantable housing has dimensions of approximately 2 mm wide by 3 mm long by 0.5 mm high.

In one embodiment, the deformable structure may include two deformable sheets welded together along opposing edges of the deformable sheets. In an alternative embodiment, the deformable structure may be formed by a single flexible sheet working against a cavity formed by a rigid chamber. The spring may be a spiral spring or a cantilevered structure. In addition, a set screw optionally may be provided that enables the implantable device to be adjusted non-invasively. For example, the set screw may be disposed on the housing and include a magnetic head configured to be magnetically coupled to an external wand that permits the set screw to be rotated to adjust the working range of the spring.

Methods of implanting, operating and adjusting the implantable device of the present invention also are provided.

BRIEF DESCRIPTION OF THE DRAWINGS

The above features and advantages of the present invention will be apparent upon consideration of the following detailed description, taken in conjunction with the accompanying drawings, in which like reference characters refer to like parts throughout, and in which:

FIG. 6 is graph showing the working range of the implantable device as a function of intraocular pressure and distal pressure.

FIG. 7 is a schematic cross section of an alternative embodiment of the implantable device of the present invention.

FIGS. 8A and 8B illustrate, respectively, symmetric pressing and asymmetric embodiments of pressing elements suitable for use in the implantable device of the present invention.

FIGS. 9A through 9C illustrate various embodiments of deformable structures suitable for use in the implantable device of the present invention.

FIG. 10 is a perspective view of a preferred embodiment of a deformable structure for use in the implantable device of the present invention.

FIGS. 11A and 11B are schematic cross sections of another alternative embodiment of the implantable device of the present invention.

FIG. 12 is a schematic cross section of a further alternative embodiment of an exemplary implantable device employing a non-invasively adjustable screw set.

DETAILED DESCRIPTION

In accordance with the principles of the present invention, an implantable device is provided to treating excessive intraocular fluid that is based upon the concept of a Starling resistor. Generally, flow through Starling resistor is determined by the interaction between a substantially constant spring force applied to a deformable tube and pressures applied at the inlet and outlet ends of the deformable tube. In a preferred embodiment, implantable device includes a deformable structure that is self-regulating to control the flow of aqueous humor from an anterior chamber of the eye, through the deformable structure, to a sink outside the eye (e.g., a bleb formed under a scleral flap or the orbital fat space of the eye). The deformable structure may be a tube, or more preferably, comprises two flat sheets welded along opposite sides to form a tube so that the sheets collapse towards one another with negligible bending moment. In an alternative embodiment, a clinician may periodically and non-invasively adjust a working range of the Starling resistor within the implantable device to maintain intraocular pressures within a desired range, thereby reducing the risk of damage to the optic nerve without requiring re-operation.

The device of the present invention is expected to provide a number of advantages over the previously-known devices and methods, including:

self-regulating pressure within the device to adapt to pressure changes either in the interior chamber of the eye, or distally at the output;

limiting the increase of IOP as a result of an increase of downstream pressure due to development of fibrosis;

limiting the decrease of IOP to avoid hypotony, especially during the time period shortly following implantation of the implantable device;

non-invasive adjustment of the working range of the spring, and accordingly the fluidic resistance of the implantable device over a wide range of values, thereby enabling IOP to be maintained within desired limits over extended periods of time;

the ability to provide patient-specific adjustments with a simple office visit to a clinician, during which the working range of the spring, and thus hydraulic resistance of the device, may be readily adjusted according to patient need; and a low volume design that facilitates implantation under a relatively small scleral flap or simply on the scleral surface, or even within a diffuser plate.

Figure 1:
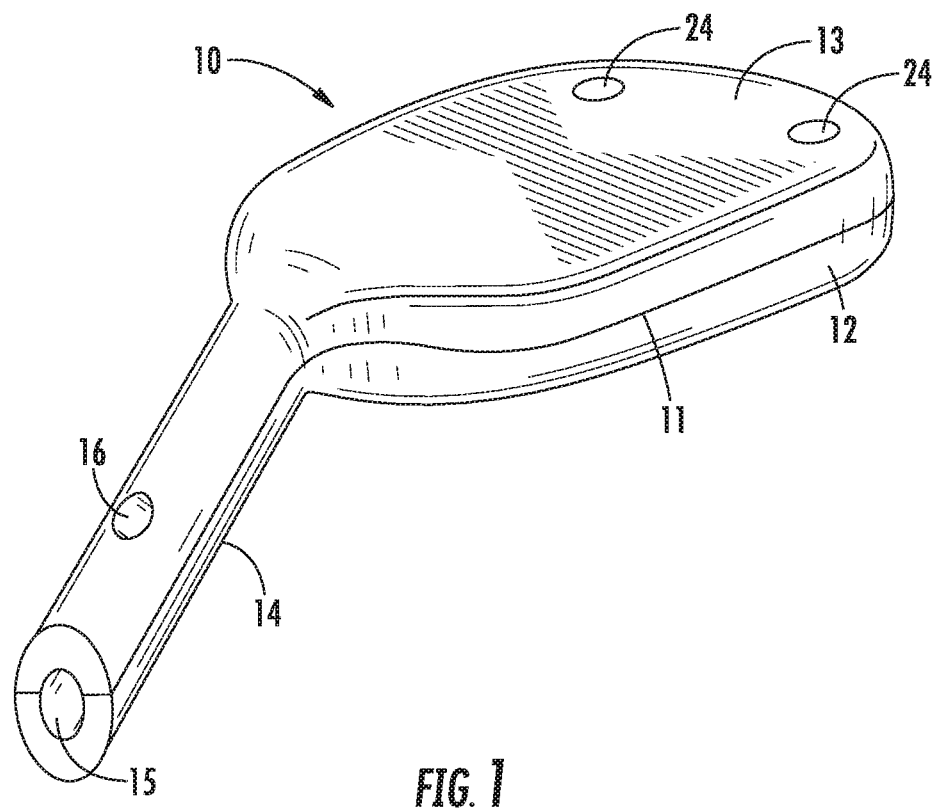
FIG. 1 is a perspective view of an implantable device constructed in accordance with the principles of the present invention.
Figure 2:
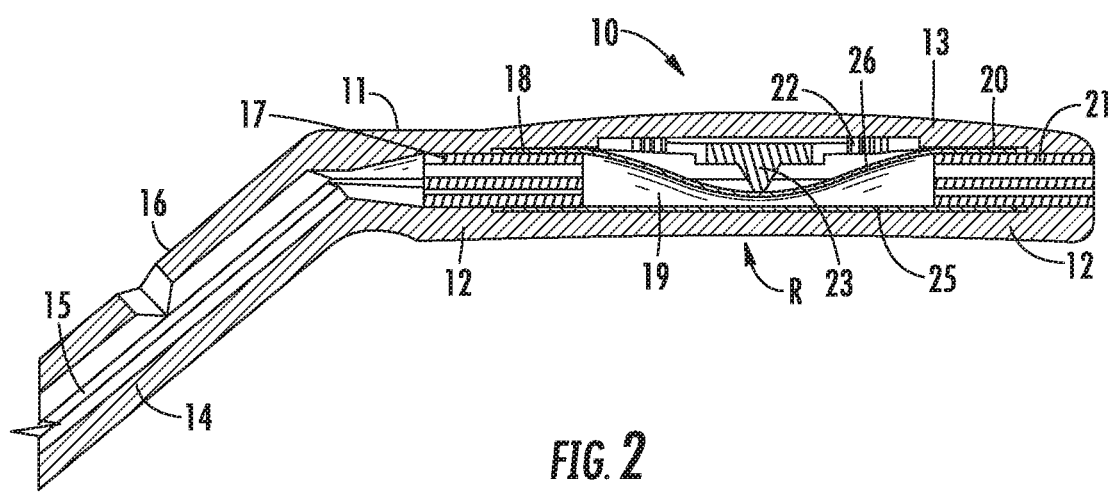
FIG. 2 is a side sectional view of the implantable device of FIG. 1.

Referring now to FIGS. 1 and 2, an implantable device of the present invention for treating excessive intraocular pressure is described. Implantable device 10 comprises housing 11 having lower portion 12, upper portion 13 and nozzle 14. The exterior surface of lower portion 12 may include a concave recess having a radius of curvature R that approximately matches the radius of curvature of the patient's eye, while the exterior surface of upper portion 13 may exhibit a correspondingly convex shape. Inlet nozzle 14 illustratively includes inlet ports 15 and 16 that communicate with inlet conduit 17. Inlet conduit 17 is in fluid communication with inlet end 18 of deformable structure 19, e.g., tube or envelope formed by joining two flat sheets along opposite sides. Outlet end 20 of deformable structure 18 is disposed in fluid communication with outlet conduit 21. Fluid passing through outlet conduit 21 is deposited with a bleb formed in the sclera of the patient's eye (see FIG. 3). Spring 22, illustratively a spiral spring having a rectangular section, is disposed within housing 11 and coupled to pressing element 23. Pressing element 23 applies a substantially contact force to deformable structure 19 over a predetermined working range, as explained herein below.

Figure 3:
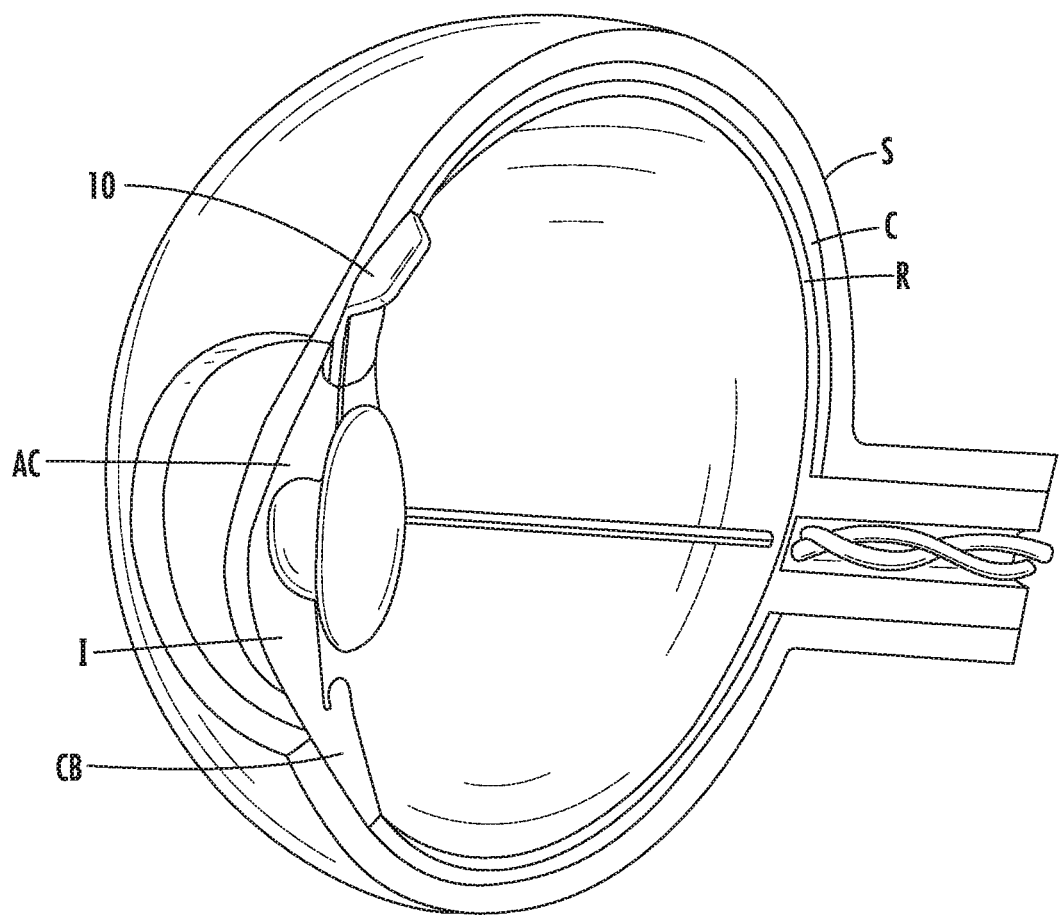
FIG. 3 is a perspective view of the implantable device of FIG. 1 implanted within a human eye.

Referring now also to FIG. 3, human eye E is depicted having anterior chamber AC, ciliary body CB, iris I, sclera S, choroid C and retina R. Nozzle 14 is configured to extend through the wall of the eye and into the anterior chamber when housing 11 is implanted beneath a flap formed in a patient's sclera. Housing 11 may include eyelets 24 that enable implantable device 10 to be sutured to the sclera to retain housing 11 in position once implanted. Flow exiting through outlet conduit 21 is deposited within the sclera, where it drains primarily to the connecting vein network. Alternatively, a surgeon may make a second scleral flap with a large cavity beneath it (a bleb) and then form a channel to connect the scleral cavity holding the implantable device to the second cavity. In this case, aqueous humor exiting the outlet conduit will flow via the channel to the second cavity, where it will be absorbed. Alternatively, flow exiting through outlet conduit 21 drains directly to the suprachoroidal space between the sclera and the choroid of the eye.

Still referring to FIGS. 1 and 2, deformable structure 19 defines a lumen having a flow area and a corresponding fluidic resistance in its undeformed state. Deformable structure 19 preferably is constructed of a flexible biocompatible material that requires very small level of force to deform and possesses negligible bending moment. In a preferred embodiment, the deformable structure comprises a tube formed by bonding two flexible flat sheets of biocompatible material 25 and 26 along opposing edges, such that the deformable structure deforms at a level of force negligible compared to the forces induced by fluid pressure within the deformable structure.

Spring 22 is disposed within housing 11 and may be affixed to upper portion 13 of housing 11. Spring 22 is configured to provide a constant, or nearly constant, force on deformable structure 19 over a predetermined working range of the implantable device. Spring 22 illustratively comprises a spiral wound spring having a rectangular cross section, and may be made, for example, from a metallic sheet. Alternatively, spring 22 may take the form of a cantilevered beam. Pressing element 23 may be coupled to spring 22 to apply force on deformable structure 19, and may have either a symmetric or asymmetric geometry.

Alternatively, spring 22 may be configured to act directly on deformable structure 19, such that pressing element 23 is entirely omitted. However, depending on the material of which deformable structure 19 is made, it is possible that friction and/or wear imposed on deformable structure 19 by constant, or nearly constant, force applied by spring 22 may pose a potential failure mechanism. Accordingly, in preferred embodiments, pressing element 23 is employed to reduce shear forces applied to the exterior of deformable structure 19.

Housing 11 preferably has dimensions of approximately 2 mm wide by 3 mm long by 0.5 mm height, and comprises a biocompatible, waterproof or water-resistant plastic such as polyether ether ketone ("PEEK"), polycarbonate or titanium. The use of PEEK or similar polymer is particularly desirable, as such polymers provide good biocompatibility and long-term structural stability when implanted.

Implantable device 10 is configured to be implanted within a scleral flap, which may be formed using techniques as commonly known in the field of glaucoma filtration surgery. The human eye is generally spherical, having a radius of curvature of approximately 11 mm. While implantable device 10 may be fabricated as a flat device, advantageously housing 11 includes a concave recess on the exterior of lower portion 12 and convex shape on the exterior of upper portion 13, each having a curvature that approximates that of the human eye so that implantable device 10 will lie snugly against the exterior of the eye beneath a scleral flap. Preferably, the radius of curvature R of lower portion 12 of housing 11 is in a range of about 10 mm to about 12 mm, and more preferably about 11 mm.

To facilitate the introduction of nozzle 14 into the anterior chamber of the eye, nozzle 14 may have a conical or sharpened extremity that facilitates piercing of the scleral tissue and introduction of the nozzle into the anterior chamber. Nozzle 14 preferably is inclined at angle $\theta$ with respect to the plane of lower portion 12 of housing 11 to facilitate insertion of the nozzle into the anterior chamber. Angle $\theta$ is selected to ensure that nozzle 14 does not contact or interfere with the iris when implanted, and preferably lies in the range of about 120° to 160°, and more preferably about 140°.

Still referring to FIG. 3, implantable device 10 is implanted within eye E, e.g., under scleral flap S, in a manner similar to previously-known glaucoma drainage devices. Aqueous humor from the anterior chamber of the eye enters device 10 via inlet ports 15 and 16, passes through inlet conduit 17, deformable structure 19 and outlet conduit 21 to the exterior of the eye, typically inside a cavity formed by the scleral flap cavity. In accordance with the principles of the present invention, the rate of drainage, and consequently, the TOP, depends on the fluidic resistance of deformable structure 19.

Advantageously, aqueous humor drained from the eye flows only through the interior of deformable structure 19, while compressive force is applied to the exterior of deformable structure 19 by spring 22. This configuration ensures that proteinaceous materials contained within the aqueous humor passing through implantable device 10 cannot create deposits on spring 22, and thus reduces the risk of component failure and blockage of implantable device 10.

Figure 4:
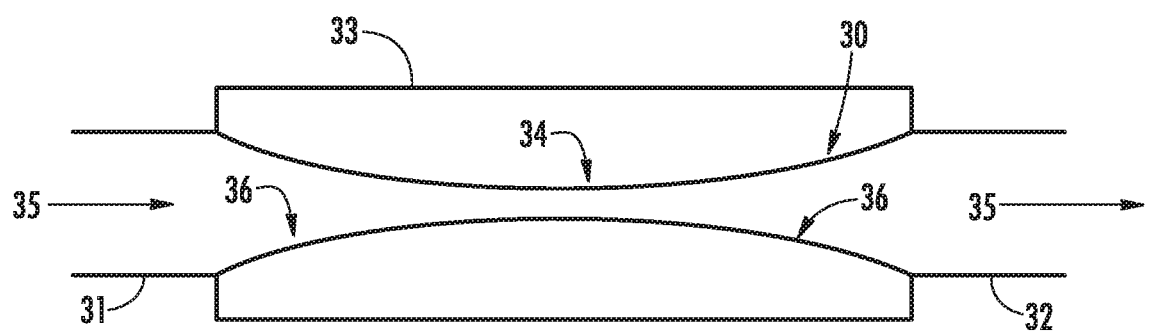
FIG. 4 is a schematic diagram of a Starling resistor.

Referring now to FIG. 4, operation of a classic Starling resistor system is described. A Starling resistor generally comprises flexible tube 30 having inlet 31 and outlet 32 disposed within cavity 33 that applies pressure 34 on the exterior of the tube. Fluid flow 35 from inlet 31 to outlet 32 applies pressure 36 to the interior of flexible tube 30. A Starling resistor is based on the phenomenon that if internal pressure 36 within flexible tube 30 is lower than external pressure 34 applied on the exterior of the tube, the tube will collapse, thereby increasing its hydraulic resistance. Ideally, the flexible tube should have negligible bending moment, so that low forces applied to the tube by external pressure 34 will deform the tube. For a given flow 35 through tube 30, the Starling resistor becomes an upstream pressure regulator in the sense that, if fluidic pressure 36 drops, the tube will collapse under the influence of external pressure 34 and the hydraulic resistance will increase. In this case, the pressure at inlet 31 will increase to reach a stable level or oscillate around a given value.

Referring now to FIGS. 5A to 5D, operation of movable components of implantable device 10 of the present invention based on the foregoing Starling resistor principles is described. As discussed above with respect to FIG. 2, implantable device 10 comprises spring 22 coupled to pressing element 23, and deformable structure 19 having a lumen coupling inlet 18 and outlet end 20. Deformable structure 19 includes a portion subjected to the force of spring 22, whereby spring 22 applies pressure with constant, or nearly constant, force k over deformable structure 19. The pressure distribution in deformable structure 19 depends directly on pressure $P_{in}$ (e.g., IOP) at inlet end 18 and pressure $P_{out}$ (in the sclera) at outlet end 20. More specifically, average pressure $P_{average}$ in the area of deformable structure 19 subjected to the force of spring 22, $A_{compressed}$, can be approximated by the formula:

$$P_{average} = \frac{\int F(x) \cdot dA}{A_{compressed}} \cong \frac{P_{in} + P_{out}}{2}$$

Figure 5A:
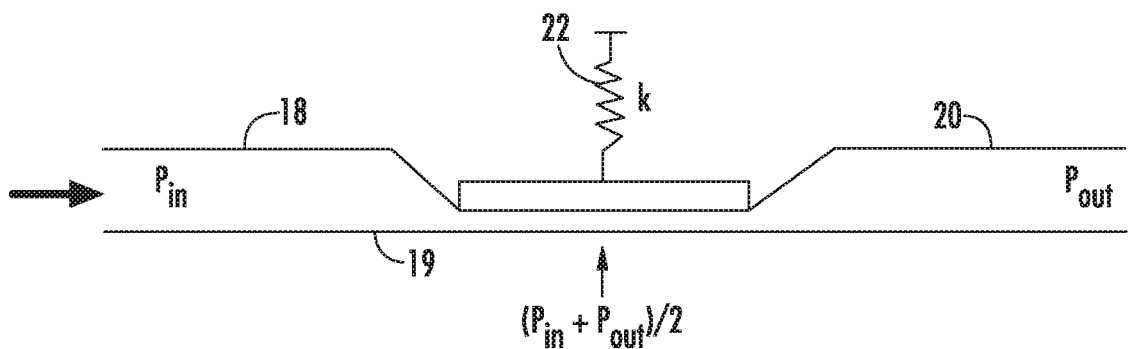
FIGS. 5A through 5D are schematic diagrams showing the geometry of the deformable structure in response to various pressure differentials between the inlet and outlet ends of the implantable device.

FIG. 5A depicts expected operation of implantable device 10 at regular IOP levels. In this case, the balance of forces between the pressure applied by spring 22 and the pressure forces within deformable structure 19 as a result of the flow of aqueous humor from the anterior chamber of the eye from inlet end 18, through deformable structure 19, and to a sink outside the eye via outlet end 20, define the geometry of deformable structure 19, its cross sectional area, and therefore its hydraulic resistance. In this case, implantable device 10 will maintain a constant desired IOP at inlet end 18 even if flow or pressure at outlet end 20 changes.

Figure 5B:
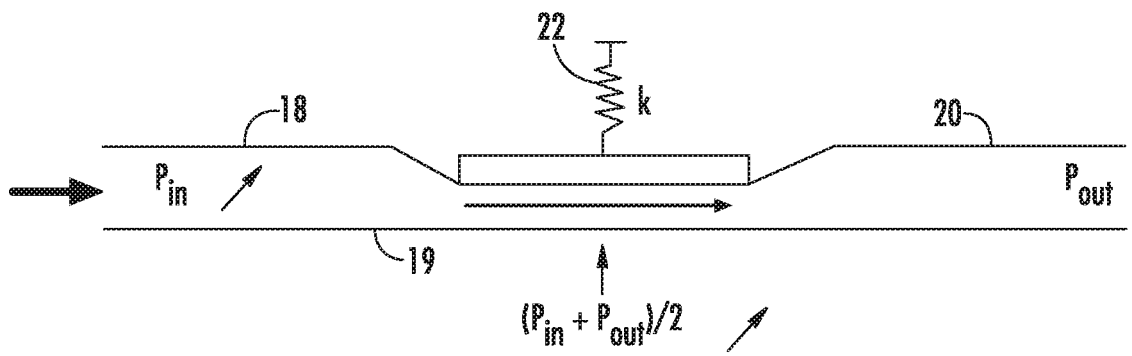

FIG. 5B illustrates expected operation of implantable device 10 when there is an increase in IOP levels at inlet end 18. For example, if flow increases, IOP will increase and the average pressure forces within deformable structure 19 will increase, which will lift spring 22, resulting in a larger flow area, smaller fluidic resistance and consequently a decrease in IOP, thereby allowing the IOP to be maintained at a pre-determined desired level. Any scenario causing IOP to increase will result in deformable structure equilibrating at a new, larger flow area and increased flow that will result in turn reduce IOP.

Figure 5C:
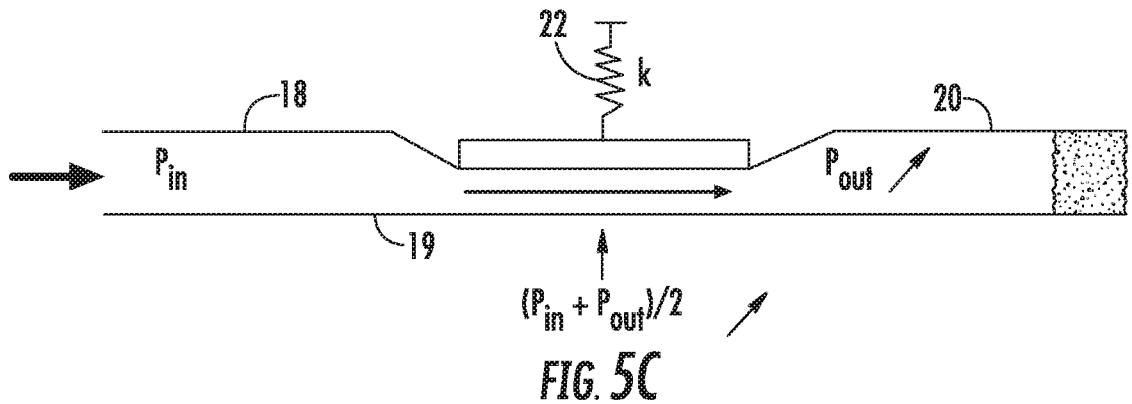

FIG. 5C illustrates expected operation of implantable device 10 when there is an increase in the pressure at outlet end 20. If pressure at outlet end 20 decreases, for example due to the development of fibrosis at outlet end 20, the average pressure within deformable structure 19 will increase, causing spring 22 to compress, which in turn will result in increased flow area and smaller fluidic resistance within deformable structure 19. Consequently, the increase of IOP at inlet end 18 will be limited.

Figure 5D:
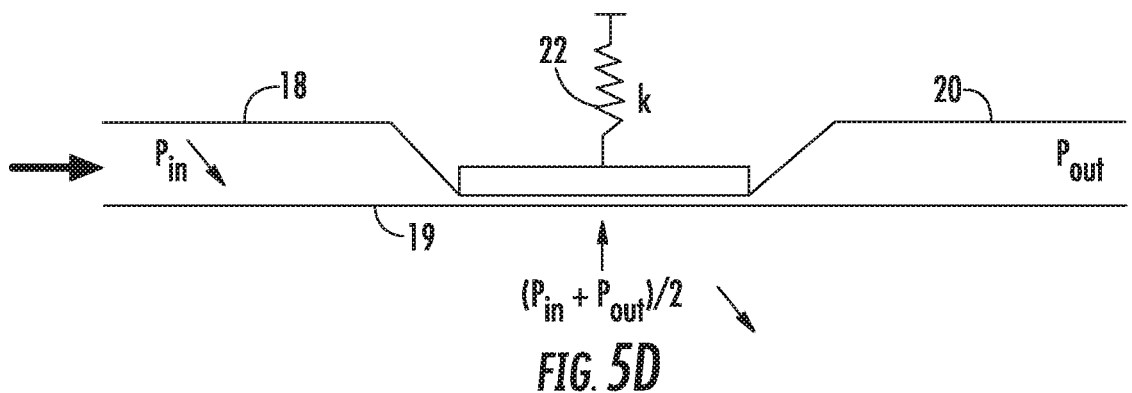

FIG. 5D illustrates expected operation of implantable device 10 when there is a decrease in IOP levels at inlet end 18. If IOP at inlet end 18 decreases, for example during the period of time right after implantation which may cause hypotony, the average pressure within deformable structure 19 will decrease, which will allow spring 22 to cause deformable structure 19 to collapse, resulting in a smaller flow area and larger fluidic resistance within deformable structure 19. This in turn will limit the decrease of IOP at inlet end 18 and reduce the risk of hypotony.

Referring now to FIG. 6, the working range of an exemplary implantable device constructed in accordance with the principles of the present invention is described. In particular, graph 40 illustrates the variation in TOP 41 as a function of pressure 42 at outlet 20 or the exit of outlet conduit 21 of implantable device 10 of the embodiment of FIGS. 1 and 2, and indicates the influence of the near constant range of the force of spring 22 on operation of the system. Working range 43 of the implantable device is defined as the region over which the force applied by spring 22 remains generally constant so that the deformable structure and spring cooperate as a Starling resistor. According to FIG. 6, working range 43 corresponds to the inflection point of the parabolic function for outlet pressure 42 ranging from 0 mm Hg up to 15 mm Hg; within that range of outlet pressures, IOP 41 varies between about 11 and 16 mm Hg. Thus, for outlet pressures 42 within the expected physiologic range, IOP 41 will be maintained around desired pre-determined levels as outlet pressure increases, even in the presence of long term fibrosis that does not result in total occlusion of the outlet.

In accordance with one aspect of the invention, the force applied by the spring depends linearly on the extent of compression or extension, such that the spring applies a constant, or nearly constant, force over the working range of the implantable device. In one preferred embodiment, the spring has a substantially contracted shape, such that small displacements of the spring, such as when the internal pressure distribution within the deformable structure increases or decreases, have negligible effect on the force applied by the spring. Alternatively, the spring may be annealed such that its deformed, extended state, is its zero-stress state. In this case, the spring may be configured to provide the desired near constant force when compressed. Preferably, for either embodiment, any spring displacement within the working range of the implantable device should be small compared to the compression length of the spring, and accordingly, any change in the force applied by the spring resulting from such small displacements should be negligible.

With respect to FIG. 7, an operative portion of an alternative embodiment of the implantable device of the present invention is described. Implantable device 50 includes upper housing 51, lower housing 52, deformable structure 53, inlet conduit 54, outlet conduit 55, spring 56 and pressing element 57. It will be understood that the foregoing components may be assembled in a housing having a nozzle substantially as described above with respect to the embodiment of FIGS. 1 and 2. It also should be understood that implantable device 50 operates as a Starling resistor within a predetermined working range in which the force applied by spring 56 to deformable structure 53 is near constant, as described above.

Implantable device 50 differs from the preceding embodiment in that spring 56 is a coiled spring, and may have a circular cross section, as compared to the spiral wound, rectangular cross section of the embodiment of FIGS. 1 and 2. In addition, pressing element 57 is mounted directed below spring 56, while the upper end of spring 56 is affixed to the interior face of upper housing 51. As for other embodiments of the implantable device, aqueous humor flow through implantable device 50 is confined to the internal lumens of deformable structure 53, inlet conduit 54 and outlet conduit 55 to reduce the risk that proteinaceous solids in the aqueous humor can deposit on and/or interfere with proper functioning of spring 56. It should be understood of course, that other types of springs could be employed in the implantable device other than spiral wound or coil springs, and that the present invention encompasses, for example, cantilever springs, Bellville (disk) springs, etc., so long as such springs have a range over which the applied force is nearly constant.

In FIGS. 8A and 8B, alternative embodiments of a pressing element suitable for use in the implantable device of the present invention are described. FIG. 8A shows symmetric pressing element 60 having centrally disposed protuberance 61, such that the force applied by the spring to deformable structure 62 (indicated by $F_{spring}$) creates a narrow constriction in deformable structure 63 with minimal force. FIG. 8B shows an alternative pressing element 65 having asymmetric protuberance 66, such that the force applied by the spring to deformable structure 67 (indicated by $F_{spring}$) is off-center and creates a longer constriction zone in the deformable structure. In the embodiment of FIG. 8B, the force created by the internal pressure distribution within the deformable structure could be more or less dependent on the inlet and outlet pressures experienced by the implantable device. In particular, FIG. 8B illustrates that pressing element 65 with asymmetrical protuberance 66 causes the vertical forces induced by the pressure within the deformable structure to become more dependent on the inlet pressure and less dependent on the outlet pressure applied to the implantable device.

Referring now to FIGS. 9A to 9C, various possible configurations of deformable structures suitable for use in the implantable device of the present invention are described. In each of these deformable structures 70, 75 and 76, the respective bending moments are negligible compared to the forces induced by the internal pressure within the deformable structures. More specifically, in FIG. 9A, deformable structure 70 comprises two polymer sheets 71 and 72 welded together along opposing edges. In this embodiment, the deformable structure may be flat in its zero-stress state and inflates when filled with fluid. In FIG. 9B, deformable structure 75 comprises an oval-shaped tube with thin walls. In FIG. 9C, deformable structure 76 comprises a circular tube with thin wall. In preferred embodiments, the deformable structures, as well as the inlet conduit and the outlet conduit, comprise of a thermosetting polymer, for example polyurethane, such that the components may be welded together by heating or by other appropriate means, such as ultrasound or RF welding.

FIG. 10 depicts an example of preferred deformable structure 80 constructed as described above for the embodiment of FIG. 9A. In particular, deformable structure 80 comprises two substantially flat polyurethane sheets 81 and 82 welded together along opposite edges 83 and 84. Sheets 81 and 82 also are welded together along inlet end 85 and outlet end 86 where deformable structure 80 is coupled to inlet conduit 87 and outlet conduit 88. As will be understood, the protuberance of a pressing element, such as pressing element 23 in the embodiment of FIG. 2, is arranged to contact central portion 89 of deformable structure 80, as that portion of the deformable structure is least effected by bending moments and end effects that may occur near edges 83 and 84 and where the deformable structure is coupled to inlet conduit 85 and outlet conduit 86.

FIGS. 11A and 11B depict a further alternative embodiment of a deformable structure and a pressing element suitable for use in the implantable device of the present invention. In this embodiment, implantable device 90 comprises rigid chamber 91 having flexible membrane 92 coupled thereto, and spring (not shown) is coupled to pressing element 93. Rigid chamber 91 extends between an inlet conduit and outlet conduit (not shown) so that the lumens of the inlet conduit and outlet conduit are in fluid communication with space 94 defined by the walls of rigid chamber 91 and flexible membrane 92, similar to the preceding embodiments of the implantable device of the present invention. Flexible membrane 92 covers rigid chamber 91 and preferably is sealed so that fluid enters and exits space 94 only via the inlet conduit and the outlet conduit. The spring preferably is configured to apply a constant, or nearly constant, force on flexible membrane 92 through pressing element 93, thereby affecting the hydraulic resistance of rigid chamber 91 in accordance with the concepts of a Starling resistor. The structure and composition of the spring may be as described above for preceding embodiments.

Referring now to FIG. 12, a further alternative embodiment of the implantable device of the present invention is described, which is designed to be periodically, non-invasively adjusted to maintain the spring force within a desired working range. More specifically, operational components of the embodiment of FIG. 12 similar to those of the embodiment of FIG. 7, are identified by like-primed numbers. Thus, for example, implantable device 50' of FIG. 12 corresponds to implantable device 50 of FIG. 7, upper housing 51' corresponds to upper housing 51, lower housing 52' corresponds to lower housing 52, deformable structure 53' corresponds to deformable structure 53, etc.

Implantable device 50' differs from implantable device 50 in that spring 56' is affixed to screw 100, which has threaded portion 101 engaged in threaded hole 102 of upper housing 51'. Screw 100 also includes magnetic head 103, which may be magnetically coupled to a magnetic wand through the overlying scleral layer once implantable device 50' is implanted. Accordingly, rotation of the magnetic wand when coupled to magnetic head 103 of screw 101 adjusts the length of the screw that extends beneath the interior surface of upper housing, thereby adjusting the elongation of, and force applied by, spring 56' upon deformable structure 53'. In this manner, the compression of spring 56' may be adjusted, and thereby, the force applied to deformable structure 53' by spring 56' may be periodically adjusted to maintain the spring force in a desired working range, as may be established with tonometry testing to determine IOP. Accordingly, the force applied to deformable structure 53' by spring 56' may be non-invasively adjusted post implantation according to patient needs, and without requiring re-operation.

Figure 13:
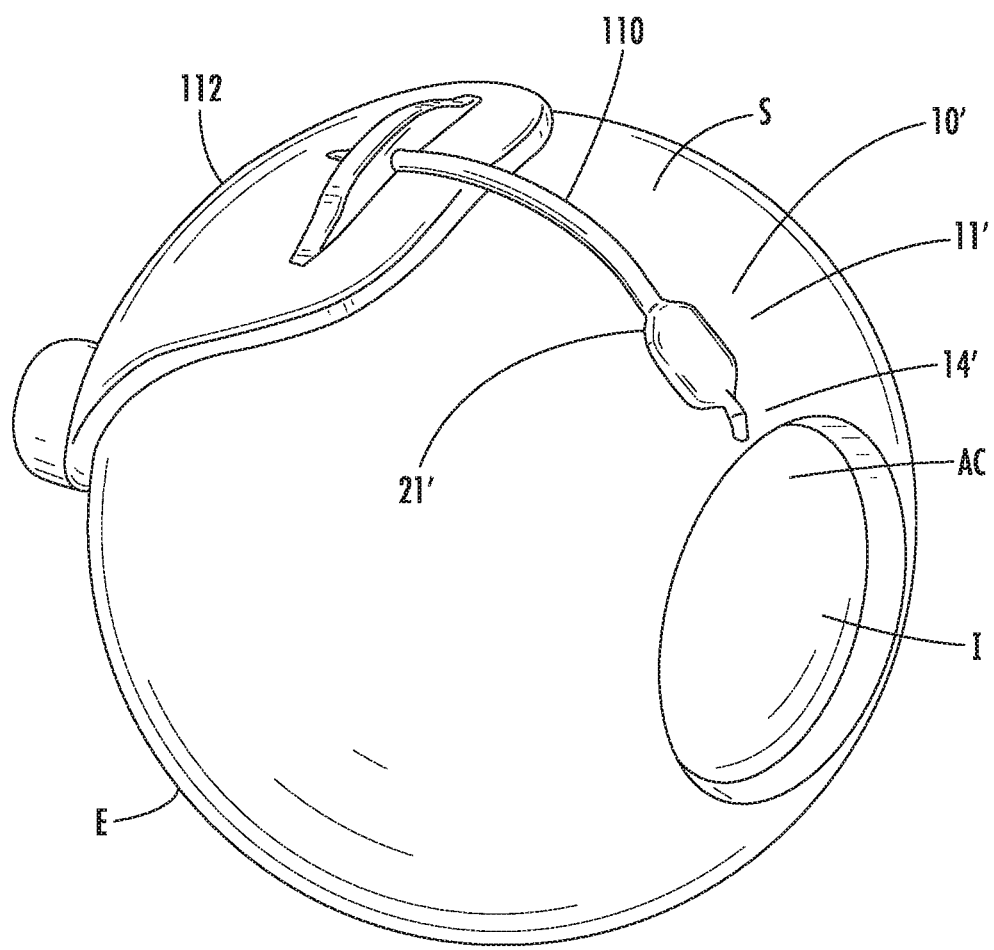
FIG. 13 is a perspective view of an alternative embodiment of the implantable device of FIG. 1 implanted above the sclera of a human eye.

Referring now to FIG. 13, an alternative embodiment of the implantable device of FIG. 1 is described, wherein the implantable device is designed to be implanted on the scleral surface of a human eye. More specifically, operational components of the embodiment of FIG. 13 similar to those of the embodiment of FIG. 1 are identified by like-primed numbers. Thus, for example, implantable device 10' of FIG. 13 corresponds to implantable device 10 of FIG. 1, nozzle 14' corresponds to nozzle 14, housing 11' corresponds to housing 11, outlet conduit 21' corresponds to outlet conduit 21, eyelets 24' corresponds to eyelets 24, etc. It also should be understood that implantable device 10' operates as a Starling resistor within a predetermined working range in accordance to any of the preceding embodiments described above.

Implantable device 10' differs from implantable device 10 in that implantable device 10' is implanted beneath the conjunctiva (not pictured), on the scleral surface of the eye. Nozzle 14' is configured to extend through the wall of the eye and into the anterior chamber. Housing 11' may include eyelets 24' (not pictured) that enable implantable device 10' to be sutured to the sclera to retain housing 11' in position once implanted. In this embodiment, a protective patch (not pictured), e.g., a layer of allograft tissue, may be positioned above the implantable device to protect the adjacent conjunctival layer from device-induced erosion. In a preferred embodiment, outlet conduit 21' of implantable device 10' may be connected to Seton tube 110 coupled to diffuser plate 112. Flow exiting through outlet conduit 21' travels through Seton tube 110 into diffuser plate 112 and is ultimately deposited within the sclera, where it drains primarily to the connecting vein network. Alternatively, in an embodiment without a Seton tube/diffuser plate combination, flow exiting through outlet conduit 21' may drain directly to the connecting vein network. Alternatively, flow exiting through outlet conduit 21' drains directly to the suprachoroidal space between the sclera and the choroid of the eye.

Figure 14A:
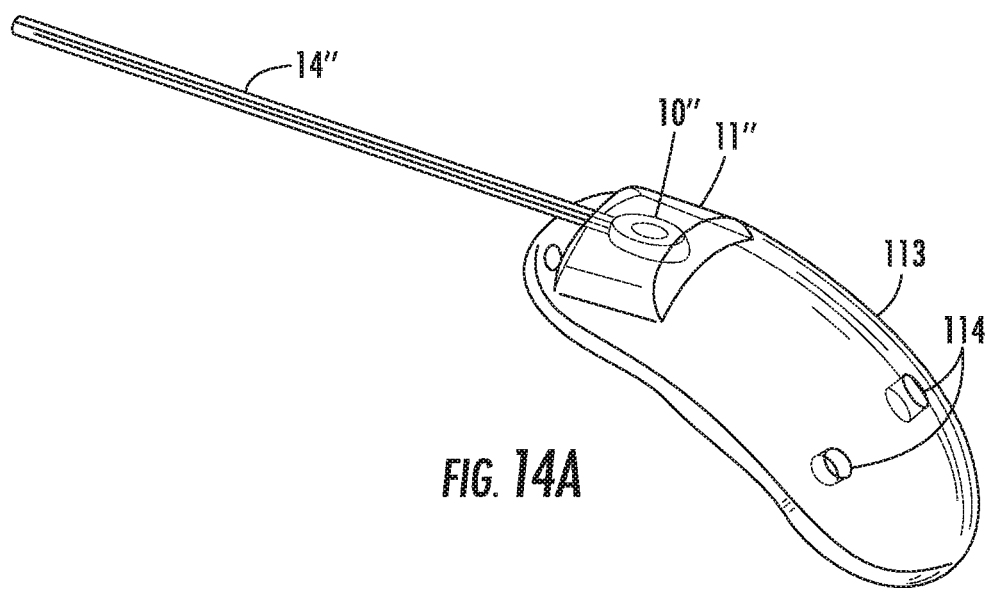
FIGS. 14A through 14C illustrate an alternative embodiment of the implantable device of FIG. 1 implanted within a diffuser plate.
Figure 14B:
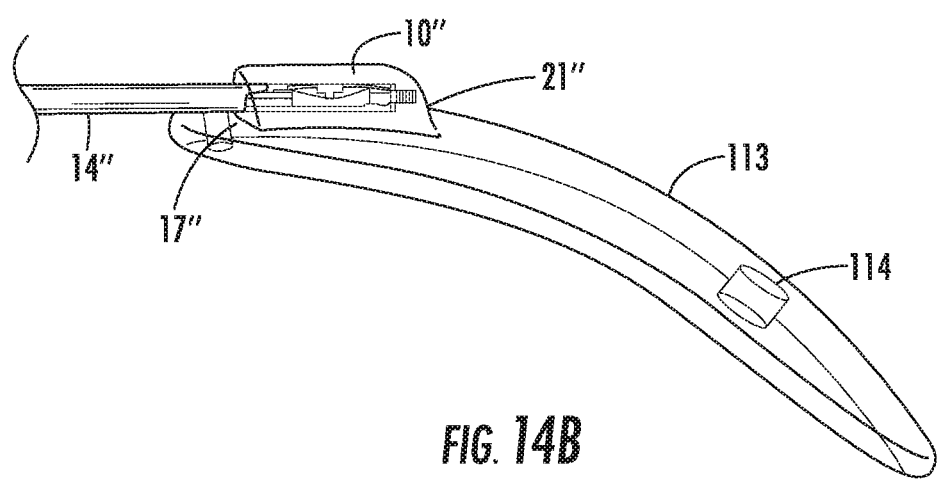
Figure 14C:
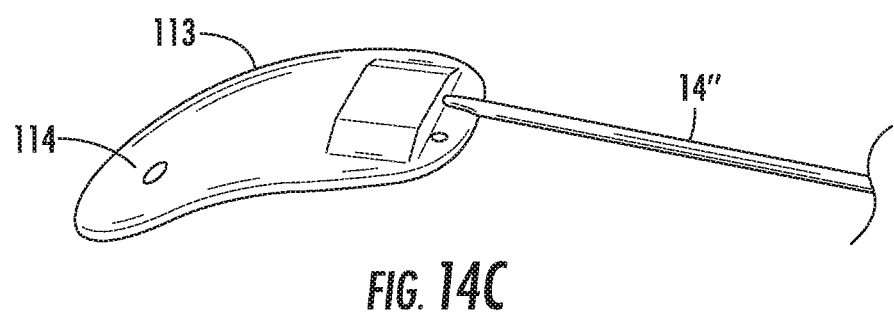

Referring now to FIGS. 14A through 14C, an alternative embodiment of the implantable device of FIG. 1 is described, wherein the implantable device is designed to be implanted within a diffuser plate on the scleral surface of a human eye. More specifically, operational components of the embodiment of FIG. 14 similar to those of the embodiment of FIG. 1 are identified by like-double primed numbers. Thus, for example, implantable device 10" of FIG. 14 corresponds to implantable device 10 of FIG. 1, nozzle 14" corresponds to nozzle 14, housing 11" corresponds to housing 11, inlet conduit 17" corresponds to inlet conduit 17, outlet conduit 21" corresponds to outlet conduit 21, etc. It also should be understood that implantable device 10" operates as a Starling resistor within a predetermined working range in accordance to any of the preceding embodiments described above.

Implantable device 10" differs from implantable device 10 in that implantable device 10" is implanted beneath the conjunctiva, on the scleral surface of the eye. In this embodiment, the implantable device is disposed within diffuser plate 113. Nozzle 14" is configured to extend from within diffuser plate 113 along the curvature of the eye and disposed through the wall of the eye and into the anterior chamber. Diffuser plate 113 may include eyelets 114 that enable diffuser plate 113 to be sutured to the sclera to retain implantable device 10" in position once implanted. Flow enters the implantable device through nozzle 14" coupled to inlet conduit 17" and exits through outlet conduit 21" into diffuser plate 113 and is ultimately deposited within the sclera, where it drains primarily to the connecting vein network.

Figure 15:
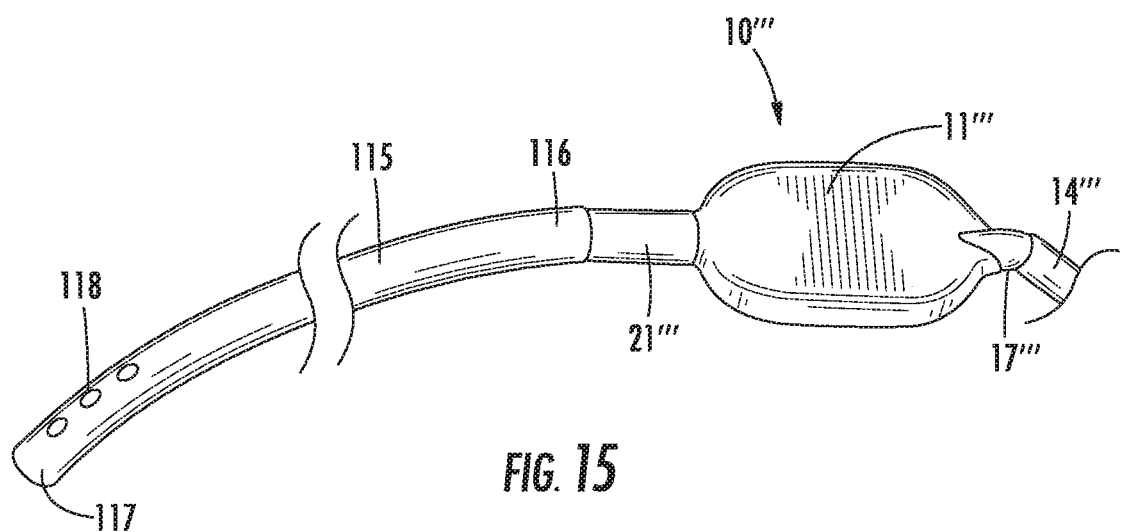
FIG. 15 illustrates an alternative embodiment of the implantable device of FIG. 1 coupled to a drainage tube.

Referring now to FIG. 15, an alternative embodiment of the implantable device of FIG. 1 is described, wherein the implantable device is designed to be coupled to a drainage tube disposed in a space, e.g., orbital fat space, of the eye. More specifically, operational components of the embodiment of FIG. 15 similar to those of the embodiment of FIG. 1 are identified by like-triple primed numbers. Thus, for example, implantable device 10' of FIG. 15 corresponds to implantable device 10 of FIG. 1, nozzle 14' corresponds to nozzle 14, housing 11' corresponds to housing 11, inlet conduit 17'" corresponds to inlet conduit 17, outlet conduit 21' corresponds to outlet conduit 21, etc. It also should be understood that implantable device 10' operates as a Starling resistor within a predetermined working range in accordance to any of the preceding embodiments described above.

Implantable device 10'" differs from implantable device 10 in that implantable device 10' is implanted beneath the conjunctiva, on the scleral surface of the eye. In this embodiment, outlet conduit 21' of implantable device 10' is coupled to proximal end 116 of drainage tube 115. Drainage tube 115 has proximal end 116, distal region 117, and a lumen extending therebetween. Proximal end 116 may be removably coupled to outlet conduit 21'" of implantable device 10'", e.g., after implantation of drainage tube 115 and after implantation of implantable device 10'". Drainage tube 115 preferably has a length such that it extends from outlet conduit 21' and distal region 117 is disposed within an orbital fat space of the eye. Distal region 117 may include one or more drainage holes 118 such that the lumen of drainage tube 115 may be in communication with the orbital fat space of the eye. Drainage tube 115 may be made of, for example, silicone, and may be sufficiently flexible to accommodate the curvature of the patient's eye.

Nozzle 14' is designed to extend from inlet conduit 17'" and be disposed through the wall of the eye and into the anterior chamber. Accordingly, flow of aqueous humor enters implantable device 10'" through nozzle 14'" coupled to inlet conduit 17'" and exits through outlet conduit 21' coupled to drainage tube 115 and is ultimately deposited within a space, e.g., orbital fat space, of the eye via one or more drainage holes 118 where it drains primarily to the connecting vein network.

Figure 16:
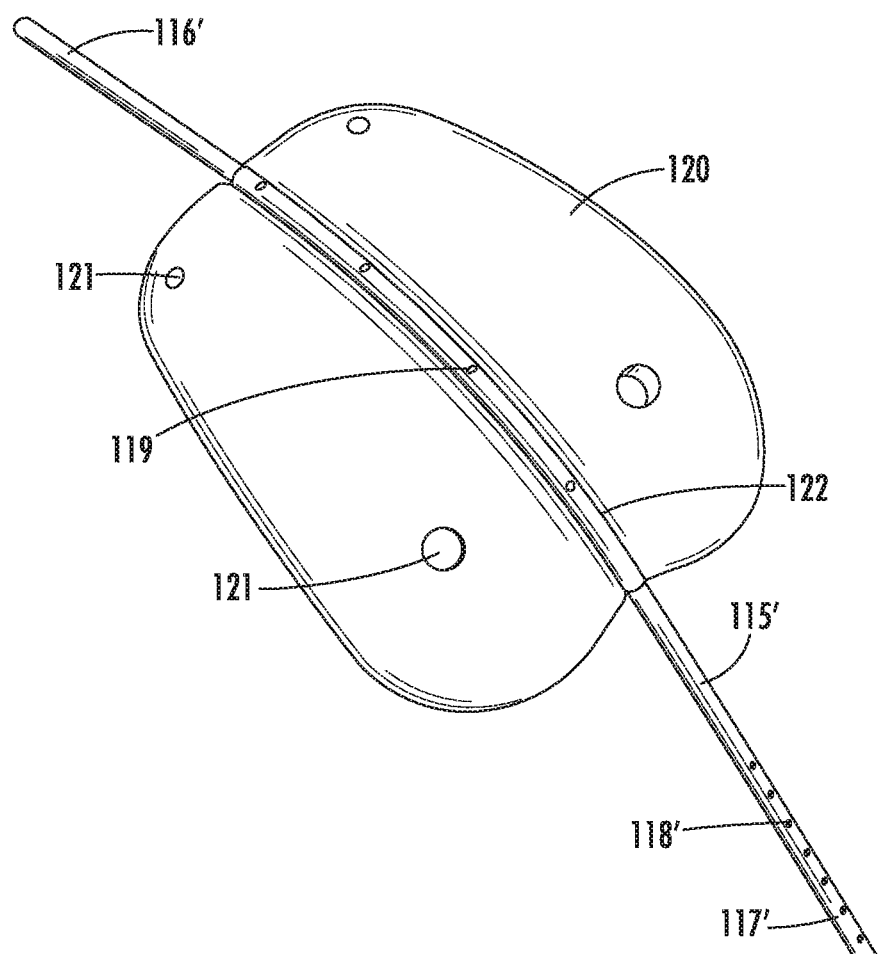
FIG. 16 illustrates an alternative embodiment of the drainage tube of FIG. 15 coupled to a diffuser plate.

Referring now to FIG. 16, yet another alternative embodiment of the implantable device of FIG. 1 is described, wherein the implantable device is designed to be coupled to a drainage tube coupled to a diffuser plate. Drainage tube 115' of FIG. 16 is constructed similar to drainage tube 115 of FIG. 15. For example, proximal end 116' and distal region 117' of drainage tube 115' of FIG. 16 corresponds to proximal end 116 and distal region 117 of drainage tube 115 of FIG. 15 respectively, and one or more drainage holes 118' of FIG. 16 corresponds to one or more drainage holes 118 of FIG. 15, etc. It also should be understood that implantable device 10'" operates as a Starling resistor within a predetermined working range in accordance to any of the preceding embodiments described above.

Drainage tube 115' coupled to diffuser plate 120 may be positioned so that diffuser plate 120 is disposed on the surface of the eye such that aqueous humor may be absorbed into the scleral tissue, e.g., into the connecting vein network, and distal region 117' of drainage tube 115' is disposed in a space, e.g., the orbital fat space, of the eye, such that aqueous humor may be absorbed into the orbital fat space of the eye. Diffuser plate 120 may be curved to accommodate the curvature of the eye and may include eyelets 121 shaped and sized to permit diffuser plate 120 to be implanted on an exterior surface of the eye via, e.g., sutures. Diffuser plate 120 may be positioned along drainage tube 115' in between proximal end 116' and one or more drainage holes 118' of drainage tube 115'. For example, diffuser plate 120 may include groove 122 shaped and sized to receive drainage tube 115', and drainage tube 115' may be maintained within groove 122 via, e.g., friction or an adhesive. In this embodiment, drainage tube 115' may include one or more drainage holes 119 along drainage tube 115' in proximity to groove 122 such that aqueous humor within the lumen of drainage tube 115' is in communication with the upper surface of diffuser plate 120. Accordingly, in an embodiment where proximal end 116' of drainage tube 115' is coupled to outlet conduit 21 of implantable device 10 of FIG. 1, aqueous humor that exits outlet conduit 21 of implantable device 10 may exit via one or more drainage holes 119 and drain over the upper surface of diffuser plate 120 into the scleral tissue, and/or exit via one or more drainage holes 118' at distal region 117' of drainage tube 115' into the orbital fat space. In this case, overall resistance of aqueous humor through drainage tube 115', e.g., due to tissue growth at either one or more drainage holes 118' or one or more drainage holes 119, may be maintained within a desired limit.

In another embodiment, the diffuser plate may be hollow such that drainage tube 115' may be positioned within the diffuser plate. In this embodiment, the diffuser plate may include one or more drainage holes along its upper surface such that the lumen of drainage tube 115' may be in communication with the upper surface of the diffuser plate.

Methods of implanting and using an implantable device constructed in accordance with the principles of the present invention are now provided. An implantable device (e.g., device 10, 50 or 50') may be implanted using a surgical technique similar to that used for prior art glaucoma drainage devices. As will be understood, for device 10 of the embodiment of FIG. 1, a scleral flap is created in a manner analogous to standard trabeculectomy, and the flap is dissected carefully up to clear cornea. The scleral flap is lifted and care is taken to identify the center of the "blue zone" adjacent to clear cornea, which corresponds to the location of the trabecular meshwork. As will be understood by one of skill in the art, the "blue zone" generally is located posterior to the anterior limbal border, and terminates in midlimbal line. A 26-gauge needle is inserted into the anterior chamber through the center of the "blue zone" at an angle parallel to the plane of the iris. Next, the nozzle of the implantable device is inserted into the anterior chamber through the ostium created by the needle until the housing lies flush against the eye. The implantable device may be secured in place within the scleral flap by applying sutures through the eyelets provided in the housing. The scleral flap then is sutured in place, e.g., using a 10-0 nylon suture with a spatulated needle. Finally the conjunctiva is carefully sutured closed to complete the implantation process.

Methods of implanting and using an alternative embodiment of the implantable device constructed in accordance with the principles of the present invention are now provided. An implantable device (e.g., device 10') is implanted using a surgical technique similar to that used for prior art glaucoma drainage devices. As will be understood, a small incision is made in the conjunctiva as an opening for the implantable device. The implantable device is positioned on the sclera surface such that the opening of the nozzle is disposed through a wall of the eye in the anterior chamber of the eye, within the aqueous humor. The implantable device may be secured in place above the sclera by applying sutures through the eyelets provided in the housing. The implantable device then may be connected to a Seton tube coupled to a diffuser plate above the sclera of the eye, a drainage tube, or a drainage tube coupled to a diffuser plate above the sclera of the eye. Optionally, a layer of allograft tissue may be sutured in place over the implantable device to reduce the risk of erosion of the adjacent conjunctival layer. Finally the conjunctiva is carefully sutured closed to complete the implantation process.

Alternative embodiments of the ocular drainage system of the present invention may include a miniaturized pressure sensor disposed with the implantable device and in communication with the inlet conduit to measure TOP. This sensor may be coupled to a miniaturized telemetry system, such as those based on radio frequency identification principles that may be energized from a distance, to emit a signal that can be received and interpreted by an external receiver. This arrangement would provide a ready way in which to non-invasively determine TOP.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A device for the treatment of excess fluid pressure within an eye, the device comprising:
   a housing configured to be implanted beneath a conjunctiva;
   a deformable tube disposed within the housing, the deformable tube having an exterior surface and a continuous lumen extending between a first end configured for fluid communication with an anterior chamber of the eye and a second end configured to be disposed beneath the conjunctiva, the deformable tube having a variable flow area; and
   a spring having a substantially constant spring force within a predetermined working range, the spring mounted within the housing to apply a force on a portion of the exterior surface of the deformable tube sufficient to self-regulate the flow of fluid through the deformable tube.

2. The device of claim 1, wherein the implantable housing has an inlet port and an outlet port, and the deformable tube extends between the inlet port and outlet port.

3. The device of claim 2, further comprising a nozzle coupled to the inlet port and configured to pass through a wall of the eye to communicate with the anterior chamber of the eye.

4. The device of claim 1, wherein the implantable housing is configured to be implanted under a scleral flap.

5. The device of claim 1, wherein the implantable housing is configured to be implanted above a sclera, the device further comprising a protective patch configured to protect a conjunctival layer from device-induced erosion, wherein the protective patch is positioned above the implantable housing.

6. The device of claim 1, further comprising a Seton tube configured to be coupled to the second end of the deformable tube.

7. The device of claim 1, further comprising a drainage tube having a proximal end configured to be coupled to the second end of the deformable tube, a distal region comprising one or more drainage holes configured to be disposed within a space of the eye, and a lumen extending between the proximal end and the one or more drainage holes.

8. The device of claim 7, wherein the one or more drainage holes are configured to be disposed within an orbital fat space such that the one or more drainage holes permit drainage into the orbital fat space.

9. The device of claim 7, further comprising a diffuser plate having a groove configured to receive a portion of the drainage tube between the proximal end and the one or more holes of the drainage tube, the diffuser plate further configured to be implanted beneath the conjunctiva and above a sclera.

10. The device of claim 1, further comprising a diffuser plate configured to be implanted beneath the conjunctiva and above a sclera, wherein the implantable housing is disposed within the diffuser plate.

11. The device of claim 1, wherein the implantable housing further comprises eyelets configured for suturing the implantable housing in a fixed position.

12. The device of claim 1, wherein the implantable housing has a radius of curvature selected to accommodate a radius of curvature of the eye.

13. The device of claim 1, wherein the deformable tube comprises a thermosetting polymer.

14. The device of claim 1, wherein the spring applies the force on a central portion of the exterior surface of the deformable tube, and wherein the force applied to the deformable tube by the spring is selected to establish a balance between an external pressure at the second end and an internal pressure of the eye at the first end.

15. The device of claim 1, wherein the deformable tube comprises two deformable sheets welded together along opposing edges of the deformable sheets, or a single flexible sheet configured to be coupled to a rigid chamber to form a cavity.

16. The device of claim 1, wherein the spring comprises a spiral spring, a coil spring, or a cantilever structure.

17. The device of claim 1, further comprising a set screw disposed on the housing, the set screw configured to be periodically moved post-implantation to adjust the spring.

18. The device of claim 17, where the set screw comprises a magnetic head configured to non-invasively adjust the working range of the spring.

19. A device for the treatment of excess fluid pressure within an eye, the device comprising:
   a housing configured to be implanted beneath a conjunctiva;
   a deformable tube disposed within the housing, the deformable tube having an exterior surface and a continuous lumen extending between an inlet end configured for fluid communication at an inlet pressure with an anterior chamber of the eye and an outlet end configured for fluid communication at an outlet pressure with a space beneath the conjunctiva, the deformable tube having a variable flow area; and
   a spring disposed within the housing to apply a force to a portion of the exterior surface of the deformable tube, the spring configured to cooperate with the deformable tube, inlet pressure and outlet pressure over a working range to form a Starling resistor that self-regulates a flow of fluid through the deformable tube.

20. The device of claim 19, further comprising a pressing element interposed between the spring and the deformable tube.

* * * * *